United States Patent [19]

Dufresne et al.

[11] Patent Number: 4,688,574
[45] Date of Patent: Aug. 25, 1987

[54] ELECTRICAL STIMULATOR FOR BIOLOGICAL TISSUE HAVING MODE CONTROL

[75] Inventors: Joel R. Dufresne, Vadnais Heights; Walter J. ReMine, St. Paul; Eric A. King-Smith, St. Louis Park, all of Minn.

[73] Assignee: Minnesota Mining and Manufacturing Company, St. Paul, Minn.

[21] Appl. No.: 744,938

[22] Filed: Jun. 17, 1985

[51] Int. Cl.⁴ .............................................. A61N 1/36
[52] U.S. Cl. .................................................. 128/421
[58] Field of Search ........................ 128/421, 422, 423

[56] References Cited

U.S. PATENT DOCUMENTS

| | | | |
|---|---|---|---|
| 3,727,616 | 4/1973 | Lenzkes | 128/422 |
| 4,255,790 | 3/1981 | Hondeghem | 128/421 |
| 4,365,290 | 12/1982 | Nelms et al. | 128/419 PG |
| 4,390,023 | 6/1983 | Rise | 128/421 |
| 4,431,000 | 2/1984 | Butler et al. | 128/421 |
| 4,476,869 | 10/1984 | Bihn | 128/419 PT |
| 4,528,984 | 7/1985 | Morawetz et al. | 128/421 |
| 4,541,432 | 9/1985 | Molina-Negro et al. | 128/421 |

OTHER PUBLICATIONS

Buckett et al., "A Flexible Portable Functional Electrical Stimulation System," 36th *ACEMB*, Sep. 12–14, 1983, p. 39.
Hogan, "Neuromuscular Stimulator Permits Customized Therapy", *Design News*, pp. 108–110, Sep. 17, 1984.
Hogan, "Tens Unit Modulates Output to Evade Body's Adaptive Capability", *Design News*, Sep. 17, 1984, pp. 114–115.

*Primary Examiner*—William E. Kamm
*Attorney, Agent, or Firm*—Donald M. Sell; James A. Smith; William D. Bauer

[57] ABSTRACT

An electrical stimulator for biological tissue having mode control. Circuit configuration parameters are stored during a certain circuit operation, such as power up. The circuit configuration parameters are checked during a second circuit configuration, such as, steady state operation and either modulated or unmodulated sets of stimulus parameters utilized to generate an electrical stimulus signal.

1 Claim, 4 Drawing Figures

4,688,574

ELECTRICAL STIMULATOR FOR BIOLOGICAL TISSUE HAVING MODE CONTROL

BACKGROUND OF THE INVENTION

The present invention relates generally to electrical stimulators for biological tissue and more particularly to electrical stimulators for biological tissue having mode control.

Electrical stimulators providing an electrical stimulus signal are useful for biological tissue. One significant use for electrical stimulators of this type is for transcutaneous electrical nerve stimulation (TENS) which generate carefully controlled electrical stimulus parameter signals which are delivered via suitable electrodes through a patients' skin to underlying biological tissue. The electrical stimulus signals may be utilized for the purpose of masking pain signals, for example, the sensation of pain felt by a patient after surgery. Because the patient's response to transcutaneous electrical nerve stimulation may vary significantly, a wide range of electrical stimulus signals must be provided. A second use of electrical stimulators is for neuromuscular stimulation (NMS) in order to initiate or control muscular contraction in a patient. Since a wide variety of muscular actions are available again a wide variety of electrical stimulus signals must be provided.

Electrical stimulators may deliver an electrical stimulus signal, which is to be applied to biological tissue, of a pulsatile nature. The pulsatile signal has a pulse amplitude, a pulse duration and a pulse frequency. The electrical stimulus signal may be varied from predetermined stimulus parameter values according to a predetermined criteria. One means to vary such stimulus parameters is to specify maximum values for pulse amplitude, pulse duration and/or pulse frequency or repetition rate. These maximum values may then be individually varied according to known criteria (such as random variation between a minimum value and a maximum value). The pulse amplitude may be varied from 100% of the specified maximum value to 60% of the specified maximum value on a random basis. Simultaneously the pulse duration may be separately, or simultaneous but independently, varied from 100% of the specified maximum value to 40% of specified maximum value on a random basis. Thus, while the maximum (or other predetermined) value of the electrical stimulus parameters are specified the actual pulses output by the electrical stimulator are likely to be only fractions of the specified maximum electrical stimulus parameter values. Such a variation of electrical stimulus parameters leads to difficulty in setting or adjusting the maximum values to an individual patients' need or comfort.

SUMMARY OF THE INVENTION

Accordingly, the present invention provides a electrical stimulator with an easy to use mode control.

In order to set or adjust the electrical stimulus parameters to an individual patient, it is desirable to have available output pulses of the electrical stimulus signal which are not varied in conjunction with such known or random criteria. When selected, such a mode would output electrical stimulus signals of a pulsatile nature with a constant stimulus parameter value set at a predetermined value, usually the maximum value. Thus, adjustment may be made utilizing such predetermined values (e.g. maximum values) knowing what the patient response is to the electrical stimulus signal at these stimulus parameter values, usually the maximum values which will not be exceeded during ordinary operation of the electrical stimulator.

Also, according to the present invention, the operator of electrical stimulator may select from more than one set of stimulus parameters. The electrical stimulator may have one set of stimulus parameters for transcutaneous electrical nerve stimulation (TENS) and one set for neuromuscular stimulation (NMS) or, alternatively, differing sets of stimulus parameters for transcutaneous electrical nerve stimulation (TENS). Thus, different modes of operation may be selected, corresponding to differing sets of stimulus parameters. The present invention provides mode control by storing circuit configuration data during a certain operating condition, such as power up, and utilizing the storage circuit configuration data, along with current circuit configuration data, to provide mode control for the electrical stimulator.

The present invention provides an electrical stimulator for biological tissue. A storage element is provided for storing a plurality of sets of stimulus parameters. A parameter variation element is operatively coupled to the storage element for varying the value of at least one of the plurality of sets of stimulus parameters according to a predetermined algorithm. A convertor is provided for converting a selected one of the plurality of sets of stimulus parameters to an electrical stimulus signal which is adapted to be supplied to biological tissue. A configuration element means is provided for recording a circuit configuration parameter of the electrical stimulator. Further, a coupling element is provided which is operatively coupled to the storage element, to the parameter variation element, to the convertor and to the configuration element. The coupling element couples a selected one of said plurality of sets of stimulus parameters to the convertor from the storage element or from the parameter variation element depending upon the circuit configuration parameters recorded in the configuration element. In a preferred embodiment, the circuit configuration parameters stored are operator control settings determined at power up of the electrical stimulator. In another preferred embodiment, the operator control setting is a switch capable of being set to at least two positions.

In a preferred embodiment of the present invention, the electrical stimulator has a coupling element which selects a first or a second one of the plurality of sets of stimulus parameters and couples the parameter variation element to the convertor when the switch is in a first position or a second position, respectively, which is the same position the switch was in during power-up of the electical stimulator. Further, the coupling element selects the second or the first one of the plurality of sets of stimulus parameters and couples the storage element to the converting means when the switch is in the first position or the second position, respectively, which is a different position from the position the switch was in during power-up of the electrical stimulator.

BRIEF DESCRIPTION OF THE DRAWINGS

The foregoing advantages, construction and operation of the present invention may be more readily understood from the following description and accompanying drawings in which.

DETAILED DESCRIPTION OF THE PREFERRED EMBODIMENTS

Figure 1:
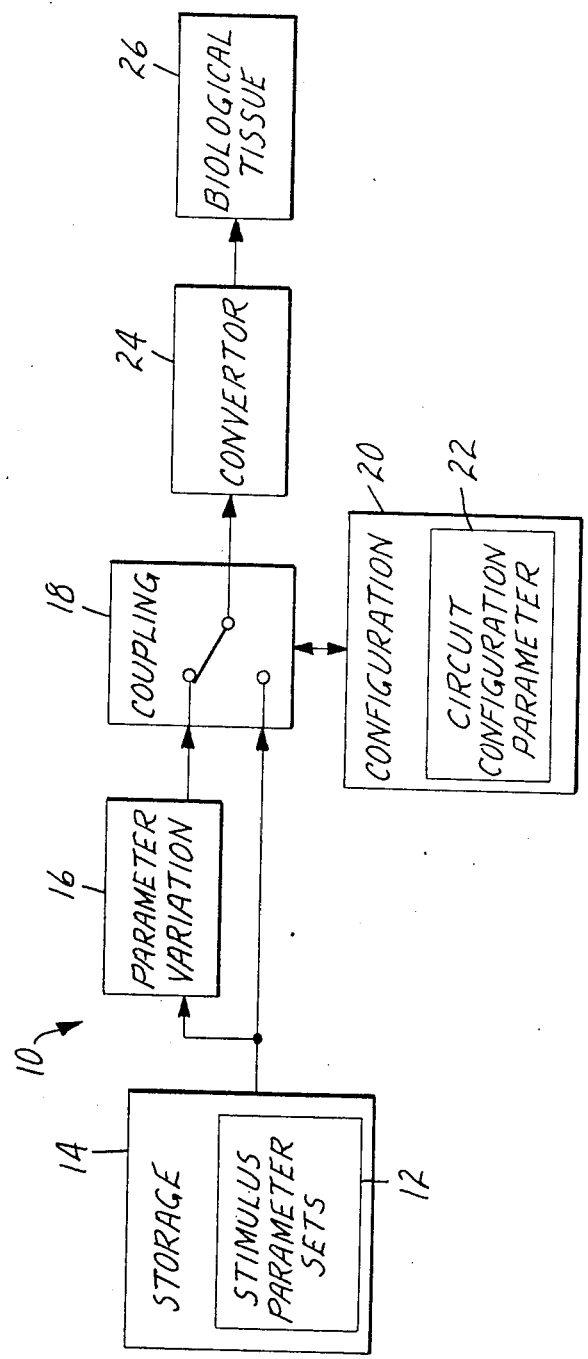
FIG. 1 is a block diagram of an electrical stimulator of the present invention along with stimulatable biological tissue.

A block diagram of the electrical stimulator 10 along with stimulatable biological tissue is illustrated in FIG. 1. A plurality of sets of stimulus parameters 12 are illustrated and stored in storage element 14. A selected one of the sets of stimulus parameters 12 provides the basic information which the electrical stimulator 10 needs to specify and generate an electrical stimulus signal. An example of the types of stimulus parameters 12 which may be stored within the storage element 14 are pulse waveform type, pulse amplitude, pulse duration and pulse frequency or repetition rate. Such stimulus parameters 12 may be varied or modulated within parameter variation element 16. One or more of the stimulus parameters 12 may be individually or simultaneously varied according to a predetermined algorithm within parameter variation element 16. An example of a variation mechanism is to specify the value of the stimulus parameters 12 as the maximum value attainable, or 100% value, of the electrical stimulus signal. A minimum value of the stimulus parameters 12 or, alternatively, a minimum percentage of the values of the stimulus parameters 12 may be specified and the parameter variation element would randomly, independently modulate stimulus parameters 12 according to a random pattern. Such randomness in modulation of stimulus parameters 12 may be advantageous in the use of the electrical stimulator 10 for transcutaneous electrical stimulation (TENS). The electrical stimulator 10 also provides unmodulated or unvaried stimulus parameters 12 from the storage element 14, as well as the modulated stimulus parameters 12 through parameter variation element 16, to a coupling element 18. The coupling element 18 selects one of the sets of stimulus parameters 12 from the storage element 14 and selects the modulated or unmodulated stimulus parameters 12 either through parameter variation element 16 or directly from storage element 14, respectively. Thus, coupling element 18 is responsible for controlling the mode of operation of electrical stimulator 10. Coupling element 18 accomplishes this function as a result of the status of configuration element 20. Configuration element 20 specifies the current condition of certain circuit configuration parameters as well as storage for past circuit configuration parameters. An example of a circuit configuration parameter which would be stored within configuration means 20 would be a user or operator controlled switch. An example of a circuit condition during which the circuit configuration parameters would be stored would be a circuit condition such as power-up of the electrical stimulator 10. Thus, the position of an operator controlled switch of the electrical stimulator 10 could be specified to be stored as a circuit configuration parameter 22 within the configuration element 20. In addition, the current position of such a switch would also be available from configuration element 20. The circuit configuration parameters 22 obtained from configuration means 20 may be utilized by coupling element 18 to select which one of the plurality stimulus parameters 12 from the storage element 14 and to select whether the modulated or unmodulated stimulus parameters 12 may be coupled through coupling element 18 and a series of digital output words indicative of the electrical stimulus signal to be generated may be supplied to converter 24. Converter 24 is then responsible for taking the series of digital output words from coupling element 18 and generating an electrical stimulus signal to be applied to biological tissue 26.

Figure 2:
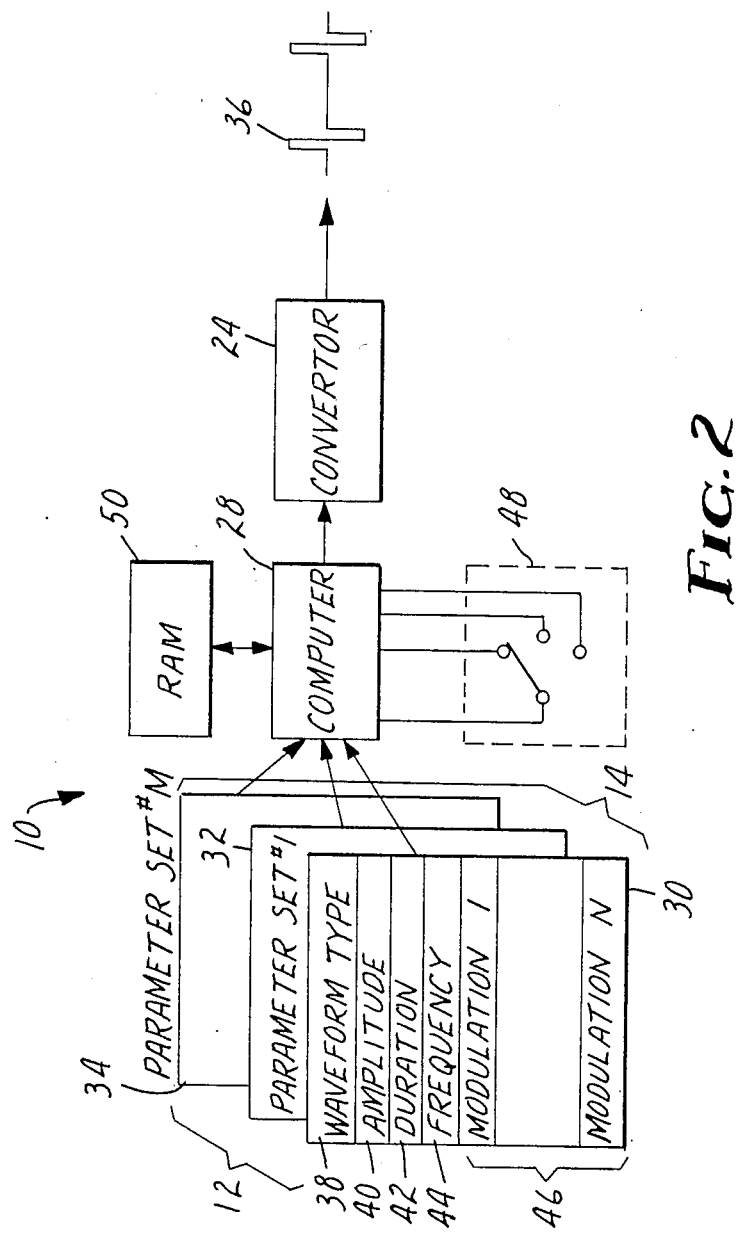
FIG. 2 is a diagram illustrating one implementation of an electrical stimulator over the present invention.

Operation of electrical stimulator 10 may be more readily illustrated by reference to FIG. 2 which describes one illustrative implementation of the electrical stimulator 10. In FIG. 2 the parameter variation element 16, and coupling element 18 have been implemented with a computer 28. Computer 28 is coupled to storage element 14 which in a preferred embodiment, consists of a randomly addressible memory. Contained within storage element 14 are a plurality of parameter sets 12 as in FIG. 1. These plurality of parameter sets 12 are diagramatically illustrated in FIG. 2 as parameter set 1 (30), parameter set 2 (32) and parameter set M (34). The number of parameter sets 12 is limited only by the capacity of storage element 14 and the addressing capabilities of computer 28. Each of the parameter sets 12 contains a specific stimulus parameter information from which the computer 28 can construct a series of digital output words to be sent to converter 24 which can convert the series of digital output words to an electrical stimulus signal 36. An example of the types of information which may be contained within a set of stimulus parameters 12 is illustrated diagramatically in FIG. 2 for parameter set 1 (30). The information contained therein may contain the waveform type 38, pulse amplitude 40, pulse duration 42, pulse frequency or repetition rate 44 and modulation factors 46. The circuit configuration element 20 of FIG. 1 is shown in FIG. 2 as mode switch 48 and randomly addressed memory 50. In a preferred embodiment, mode switch 48 consists of a two position switch under operator control. Computer 28 samples the position of mode switch 48 upon the occurrence of a certain circuit condition, such as power up of the electrical stimulator 10. This information is then stored in randomly addressable memory (RAM) 50 to provide circuit configuration parameters 22 storage in configuration element 20. The current position of mode switch 48 continues to be available to computer 28 from mode switch 48. Armed with this information, computer 28 then constructs a series of digital output words to be sent to converter 24 in order to be converted to an electrical stimulus signal 36 which may applied to biological tissue (not shown). An example of a converter 24 which may be utilized to convert a series of digital output words to an electrical stimulus signal 36 is described in a copending U.S. patent application entitled, "Electrical Stimulator For Biological Tissue Having Linear Current Output Circuit", invented by Dufresne et al, being identified as Ser. No. 06/745,212, filed June 17, 1985, and being assigned to the assignee of the present application, the contents of which are hereby incorporated by reference. Computer 28 may be any microcomputer suitable for accomplishing the task at hand but may, for example, be a model 80C49 microcomputer and associated hardware as manufactured by Intel Corporation. Storage element 14 and random access memory 50 are conventional storage elements whose sizes depend upon the particular parameter information being stored. Mode switch 48 is any commonly available switch having at least two positions under operator control.

Figure 3:
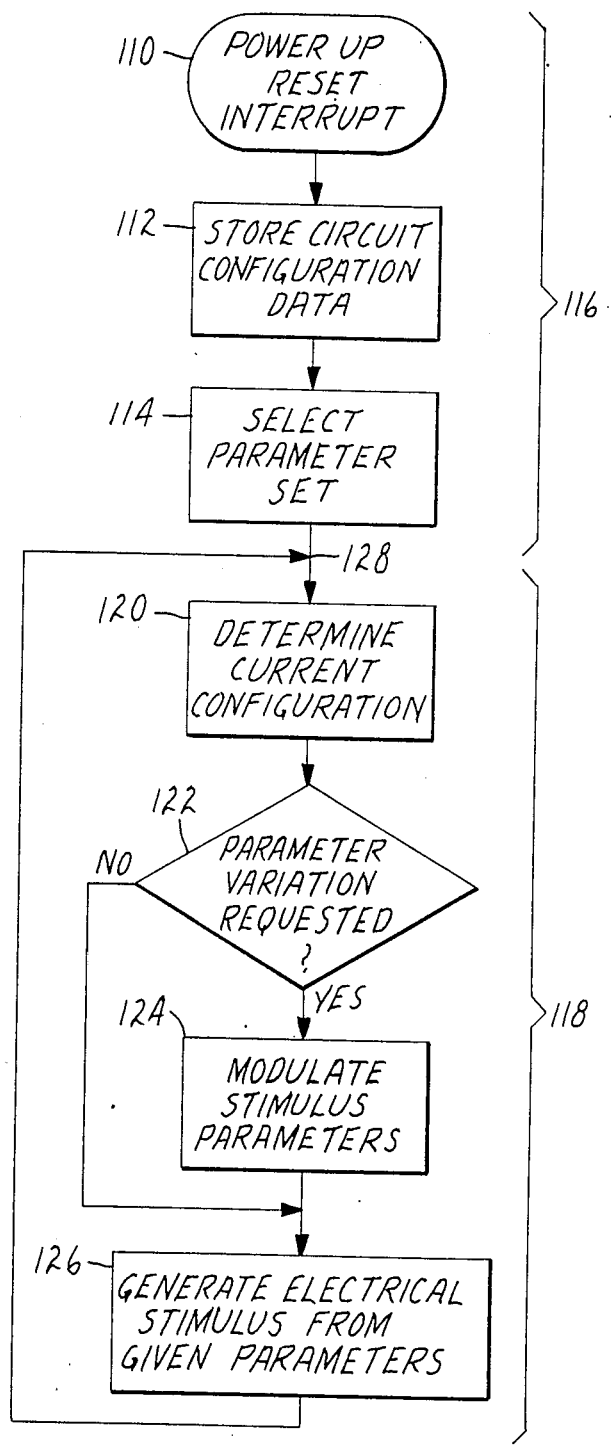
FIG. 3 is a flow diagram of a software program for controlling the microprocessor of FIG. 2.

FIG. 3 is a flow chart of the software program which operates computer 28 in order to enable computer 28 to achieve the parameter variation and coupling functions of parameter variation element 16 and coupling element 18. Given the flow chart illustrated in FIG. 3 one of ordinary skill in the art could construct a suitable microprogram for utilization with microcomputer 28 to achieve the functions illustrated. The flow chart in FIG. 3 is entered at block 110 upon the occurrence of a particular circuit event of the electrical stimulator 10. Block 110 may be entered preferably upon power-up of the electrical stimulator 10 and also perhaps upon reset of the electrical stimulator 10 or upon the occurrence of an external interrupt based on an external event. Upon the occurrence of the circuit event which caused block 110 to be entered, the program at block 112 would take the necessary steps to store the circuit configuration data in conjunction with FIG. 2. This would encompass the microcomputer 28 monitoring the position of mode switch 48 during the power-up, reset or interrupt operation and storing that data within RAM 50. Computer 28 will then select the one of the plurality of stimulus parameters 12 which will be utilized by the electrical stimulator 10. In one embodiment of the present invention, the selection of the particular set of stimulus parameters 12 to be utilized is conventional in nature and may depend upon other stored information available to the microprocessor or upon other external user specified controls. Blocks 112 and 114 are accomplished during the power-up operating state 116. The remainder of the flow diagram in FIG. 3 encompases the steady state operation 118. The program then determines the current configuration of mode switch 48 as shown in block 120. This determination is based upon both the circuit configuration parameter storage from RAM 50 and upon the current position of mode switch 48. Based upon this information, the computer 28, in block 122, determines whether stimulus parameter variation has been specified. If the answer to the question is yes, then, in block 124, the computer 28 modulates the stimulus parameters according to a predetermined algorithm. If the answer to the question is no, stimulus parameters are passed directly, block 126, and the sequence of digital output words are generated and provided to converter 24. The program then re-enters at point 128 to repeat the steady state operation 118.

Figure 4:
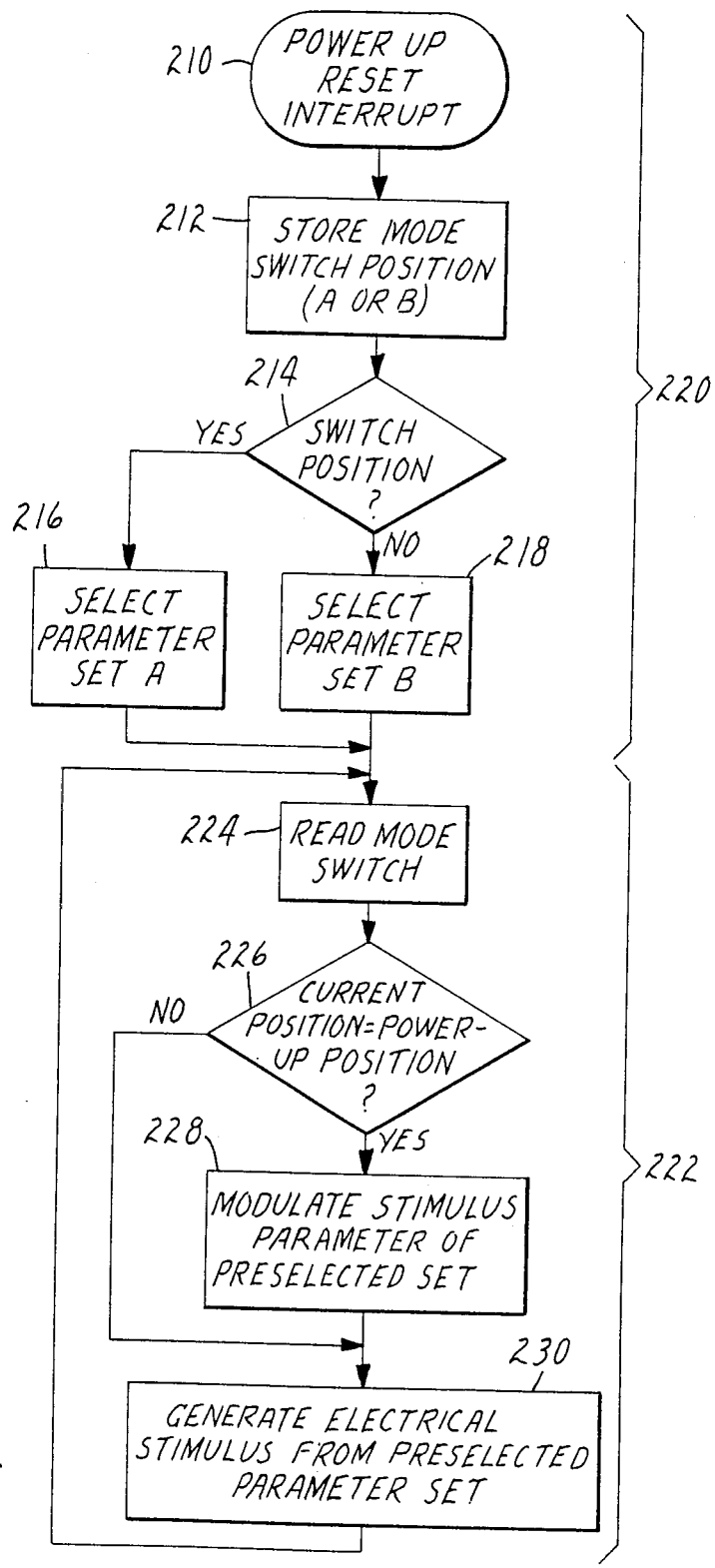
FIG. 4 is a flow diagram of a preferred embodiment of the software for controlling the microprocessor FIG. 2.

Detailed operation of the software program which may be utilized in a microcomputer 28 is illustrated in FIG. 4. Again, block 210 is entered upon the occurrence of a certain circuit configuration such as power-up, reset or interrupt. Block 212 is entered during which the program will store the position of mode switch 48 within RAM 50. In block 214, depending upon the position of mode switch 48, the program will either select parameter set A 216 or select parameter set B 218. This portion of the program operation occurs during power-up state operation 220. Then during steady-state operation 222, the program reads the current position of mode switch 48 at block 224. The program then determines whether the current position of mode switch 48 is identical to the position of mode switch 48 which was stored during operation 212. If the current position of mode switch 48 is identical to the position of the mode switch 48 during power up at block 210, then, at block 228, the program modulates the selected stimulus parameters 12 according to the predetermined alogrithm or criteria. The modulated stimulus parameters 12 from block 228 are then sent to block 230 during which the program will generate the sequence of digital output words to be sent to converter 24. Alternatively, if the current position of the mode switch 48 is not identical to the position of the mode switch 48 which was stored during power up at block 212, then the modulation operation of block 228 is bypassed and the stimulus parameters are passed unmodulated and at block 230 again a series of digital output words are constructed to be passed to converter 24. Note that in this preferred embodiment of the program to be utilized in computer 28, either the modulated or unmodulated set of stimulus parameters, is selected to have a set or sequence of digital output words generated to be sent to converter 24. In order to change between parameter set A or parameter set B, the electrical stimulator 10 must be interrupted, reset or powered up with mode switch 48 in the other position.

A preferred embodiment of a software program to generate a series of output words for convertor 24 is illustrated the flow charts contained in copending patent application by King-Smith, ReMine and Dufresne, entitled, An Output Limited Electrical Stimulator For Biological Tissue, Ser. No. 745,084, filed June 17, 1985 and assigned to the assignee of the present application, the contents of which are hereby incorporated by reference.

It is to be noted that the change in modes has been illustrated and described in conjunction with an A or B position and as described and illustrated is the function of a single two position operator control switch. It is to be recognized and understood that a plurality of modes of control of electrical stimulator 10 could be achieved with a more sophisticated mode switch 48 and with a natural extension of the selection process of selecting between parameter sets 12.

Thus, it has been shown that there has been described a novel electrical stimulator of biological tissue having mode control. It is to be recognized and understood, however, that various changes, substitutions and modifications of the present invention may be made by those skilled in the art without departing from the scope of the present invention as defined by the following claims.

What is claimed is:

1. An electrical stimulator for biological tissue, comprising:
    storage means for storing a plurality of sets of stimulus parameters;
    parameter variation means operatively coupled to said storage means for varying the value of at least one of said plurality of sets of stimulus parameters according to a predetermined algorithm;
    converting means for converting a selected one of said plurality of sets of stimulus parameters to an electrical stimulus output signal which is adapted to be supplied to biological tissue;
    an operator controlled switch settable to at least two positions;
    coupling means operatively coupled to said storage means, to said parameter variation means, to said converting means and to said configuration means, said coupling means for coupling a selected one defined by said operable controlled switch upon power-up of said plurality of sets of stimulus parameters to said converting means from said storage means or from said parameter variation means wherein said coupling means selecting a first or a second one of said plurality of sets of stimulus parameters and coupling said parameter variation means to said converting means when said switch is in a first position or a second position, respectively, which is the same position said switch as in during power-up of said electrical stimulator and wherein said coupling means is selecting said second or said first one of said plurality of sets of stimulus parameters and coupling said storage means to said converting means when said switch is in said first position or said second position, respectively, which is a different position from the position said switch was in during power-up of said electrical stimulator.

* * * * *